(12) United States Patent
Fujita et al.

(10) Patent No.: US 7,160,841 B2
(45) Date of Patent: Jan. 9, 2007

(54) UNIFORMLY SPREADABLE GRANULAR AGRICULTURAL CHEMICALS FORMULATION AND METHOD FOR SCATTERING (APPLYING) THEREOF

(75) Inventors: Shigeki Fujita, Iwata (JP); Susumu Kato, Shizuoka (JP)

(73) Assignee: Kumiai Chemical Industry Co., Ltd., Tokyo (JP)

(*) Notice: Subject to any disclaimer, the term of this patent is extended or adjusted under 35 U.S.C. 154(b) by 323 days.

(21) Appl. No.: 10/116,032

(22) Filed: Apr. 5, 2002

(65) Prior Publication Data

US 2004/0011262 A1    Jan. 22, 2004

(30) Foreign Application Priority Data

Sep. 26, 2001   (JP) ............................. 2001-293613

(51) Int. Cl.
*A01N 3/02* (2006.01)
(52) U.S. Cl. ...................... 504/367; 504/116
(58) Field of Classification Search ............... 504/248, 504/116, 323, 324, 280, 222, 344, 367; 514/951, 514/949; 71/64.03, 64.04, 64.05; 427/212, 427/213, 213.31
See application file for complete search history.

(56) References Cited

U.S. PATENT DOCUMENTS

| 5,380,350 | A | * | 1/1995 | Fersch ........................ 71/64.03 |
| 5,856,418 | A | * | 1/1999 | Maeda et al. ................. 526/304 |
| 6,486,095 | B1 | * | 11/2002 | Fujita et al. ................. 504/367 |
| 6,703,350 | B1 | * | 3/2004 | Fujita et al. ................. 504/367 |
| 6,797,674 | B1 | * | 9/2004 | Kato et al. .................. 504/367 |

FOREIGN PATENT DOCUMENTS

| JP | 48-1179 | 1/1973 |
| JP | 48-1181 | 1/1973 |
| JP | 48-1182 | 1/1973 |
| JP | 48-56831 | 8/1973 |
| JP | 55-154902 | 12/1980 |
| JP | 56-30901 | 3/1981 |
| JP | 58-65203 | 4/1983 |
| JP | 6-336403 | 12/1994 |
| JP | 6-345603 | 12/1994 |
| JP | 7-82102 | 3/1995 |
| JP | 7-101805 | 4/1995 |
| JP | 7-233002 | 9/1995 |
| JP | 9-183701 | 7/1997 |

* cited by examiner

Primary Examiner—Sabiha N. Qazi
(74) Attorney, Agent, or Firm—Oblon, Spivak, McClelland, Maier & Neustadt, P.C.

(57) ABSTRACT

An object of the present invention is to provide a uniformly spreadable granular agricultural chemical formulation and to establish a method of scattering (applying) the formulation under the assumption that the spreadability of the agrochemically active ingredient is satisfactory so that the expected treatment effect of the agricultural chemicals can be obtained by local application even when algae are drifted by the wind and cover the surface of the water of the paddy field. A uniformly spreadable granular agricultural chemicals formulation which contains an agrochemically active ingredient, has a particle-size distribution such that 80% or more of the granules have a particle diameter of 3 mm or more, and has floatability on the water surface, and breaks down on the water surface within 30 minutes is obtained, and a method of scattering (applying) the above formulation on 5% to 50% of the total area of the paddy field applied from a levee at a distance of 1 m or more.

17 Claims, 7 Drawing Sheets

UNIFORMLY SPREADABLE GRANULAR AGRICULTURAL CHEMICALS FORMULATION AND METHOD FOR SCATTERING (APPLYING) THEREOF

FIELD OF THE INVENTION

The present invention relates to a granular agricultural chemicals formulation in which an agrochemically active ingredient therein can be spread uniformly, for instance, by directly scattering (applying) the granular agricultural chemicals formulation partially on the water-surface of a paddy field or the like and a method for scattering (applying) thereof.

DESCRIPTION OF RELATED ART

Conventionally, as an agricultural chemicals formulation used in a paddy field or the like, a granular type, powder type, emulsifiable type, wettable type, and suspension type have been commonly used. The granular type and the powder type among these granular agricultural chemicals formulations are generally directly scattered (applied) at a rate of 3 kg to 4 kg per 10 are without being diluted with water. However, labor-saving scattering (applying) of agricultural chemicals has been lately demanded. In order to cope with this demand, a method of reducing the scattering (applying) amount of total agricultural formulation by increasing the content of the agrochemically active ingredient existing therein, or an agricultural chemicals formulation which can be scattered (applied) by only throwing from a levee without entering into a paddy field, has been studied.

Various agricultural chemicals formulations have been studied for such a demand, and the technologies thereof have been disclosed. For instance, disclosed are a granular agricultural chemicals formulation in which an agrochemically active ingredient is dissolved or dispersed in a wax-like substance having specific gravity of 1 or less, and coated with or contained in a water-soluble filler (Japanese Patent Laid-open No. Sho 55-154902, Japanese Patent Laid-open No. Sho 56-30901, Japanese Patent Laid-open No. Hei 7-101805), a composition in which a fungicidal active ingredient is carried by a water-floatable carrier such as pumice or pearlite (Japanese Patent Publication No. Sho 48-1179), a composition in which an insecticidal active ingredient is attached on pearlite using paraffin petroleum resin and the like (Japanese Patent Publication No. Sho 48-1181), a composition in which a herbicidal active ingredient is carried on a water-floatable inorganic carrier such as pearlite (Japanese Patent Publication No. Sho 48-1182), a granular agricultural chemicals formulation in which an agrochemically active ingredient and a water-repellant substance are carried by a granular mineral carrier having particle-size of 48 mesh or less (Japanese Patent Laid-open No. Sho 48-56831), a composition in which an agrochemically active ingredient is carried and formed by a hollow body having specific gravity of 1 or less and particle diameter of 5 mm or less (Japanese Patent Laid-open Sho. 58-65203) and the like.

However, in all of the above-described agricultural chemicals formulations, since the wax-like substance containing the agrochemically active ingredient or the granular nucleus carrying the agrochemically active ingredient floats on the water surface for a long time, unevenness in concentration of the agrochemically active ingredient is created in the paddy field due to drifting by the wind, which results in a disadvantage of obtaining insufficient effect of the chemicals and possibility of phytotoxicity.

A composition containing an agrochemically active ingredient, a specific surfactant, bentonite, and a water-floatable hollow particle (Japanese Patent Laid-open No. Hei 7-82102), and a composition containing an agrochemically active ingredient, a glass hollow body having a diameter of 250 µm or less, and a specific surfactant (Japanese Patent Laid-open No. Hei 6-345603) are disclosed. However, in order to obtain desirable breakdown, it is necessary to make the particle diameter substantially 2 mm or less, which leads to an unfavorable result affected by the wind when scattering (applying). Furthermore, a water-floatable granular formulation having a particle diameter in the range from 1 mm to 5 mm with a composition composing of an agrochemically active ingredient, a base powder having specific gravity of 1 or less, and a surfactant having a specific nature is disclosed (Japanese Patent Laid-open No. Hei 7-233002). Since this formulation has a large amount of powder base having specific gravity of 1 or less and is fragile, there arises a disadvantage in such that a person who scatters (applies) the agricultural chemicals is exposed to the chemicals when applying, or the agricultural chemicals are flown to the peripheral environment.

Futhermore, a composition containing a formulation, wrapped in a water-soluble film, composed of an agrochemically active ingredient, calcined vermiculite or foamed pearlite, foamed shirasu, cork, and an acetylene-derivative surfactant, is disclosed in Japanese Patent Laid-open No. Hei 6-336403. Since the amount of formulation of the calcined vermiculite or foamed pearlite, foamed shirasu, and cork to give the floatability on the surface of paddy water is large, the strength against compression and collapse is extremely low and easy to break down. Accordingly, when scattered (applied) directly onto a paddy field, the agricultural chemicals contained therein may be exposed to the human body and have an unfavorable effect on the peripheral environment. Therefore, this sort of agricultural chemicals is developed under the assumption that it will be thrown into a paddy field in a packed form with a water-soluble film. This kind of formulation packed with a water-soluble film, a so-called jumbo-type formulation is generally to be thrown from a levee at a rate of several pieces to about 20 pieces per 10 are of a paddy field, which makes it possible to realize the labor-saving application of agricultural chemicals. However, the fact is that sufficient diffusion of the agrochemically active ingredient can not be obtained for a recently rearranged wide paddy field, or a paddy field in which the water surface is covered with algae, so that the expected effect cannot be obtained.

SUMMARY OF THE INVENTION

The present invention is to solve the disadvantages of the agricultural chemicals formulation, which have been hitherto presented. An object of the present invention is to provide a uniformly spreadable granular agricultural chemicals formulation and to establish a method of scattering (applying) the formulation assuming that the spreadability of the agrochemically active ingredient is satisfactory so that expected treatment effect of the agricultural chemicals can be obtained by local application even when algae are drifted by the wind and cover the water surface of the paddy field.

As a result of assiduous study of a water-floatable granular agricultural chemicals formulation to allow to spread the agrochemically active ingredient uniformly, especially of its desirable physical property, the present inventors have found that the above problem can be solved by adjusting the physical properties of the granular formulation in a specific range and have accomplished the present invention.

That is, the present invention is to provide a uniformly spreadable granular agricultural chemicals formulation which contains an agrochemically active ingredient, has properties of a particle-size distribution in such that 80% or more of the granules have a particle diameter of 3 mm or more, and floats on the water surface, and breaks down on the water surface within 30 minutes.

In addition, the present invention is to provide a method of scattering (applying) a uniformly spreadable granular agricultural chemicals formulation, which contains an agrochemically active ingredient, has a particle-size distribution in such that 80% or more of the granules have a particle diameter of 3 mm or more, floats on the water surface, and breaks down on the water surface within 30 minutes, comprising the step of scattering (applying) the uniformly spreadable agricultural chemicals formulation on 5% to 50% of the total area of the paddy field applied from a levee of a submerged paddy field at a distance of 1 m or more.

DETAILED DESCRIPTION OF THE PREFERRED EMBODIMENTS

Figure 1:
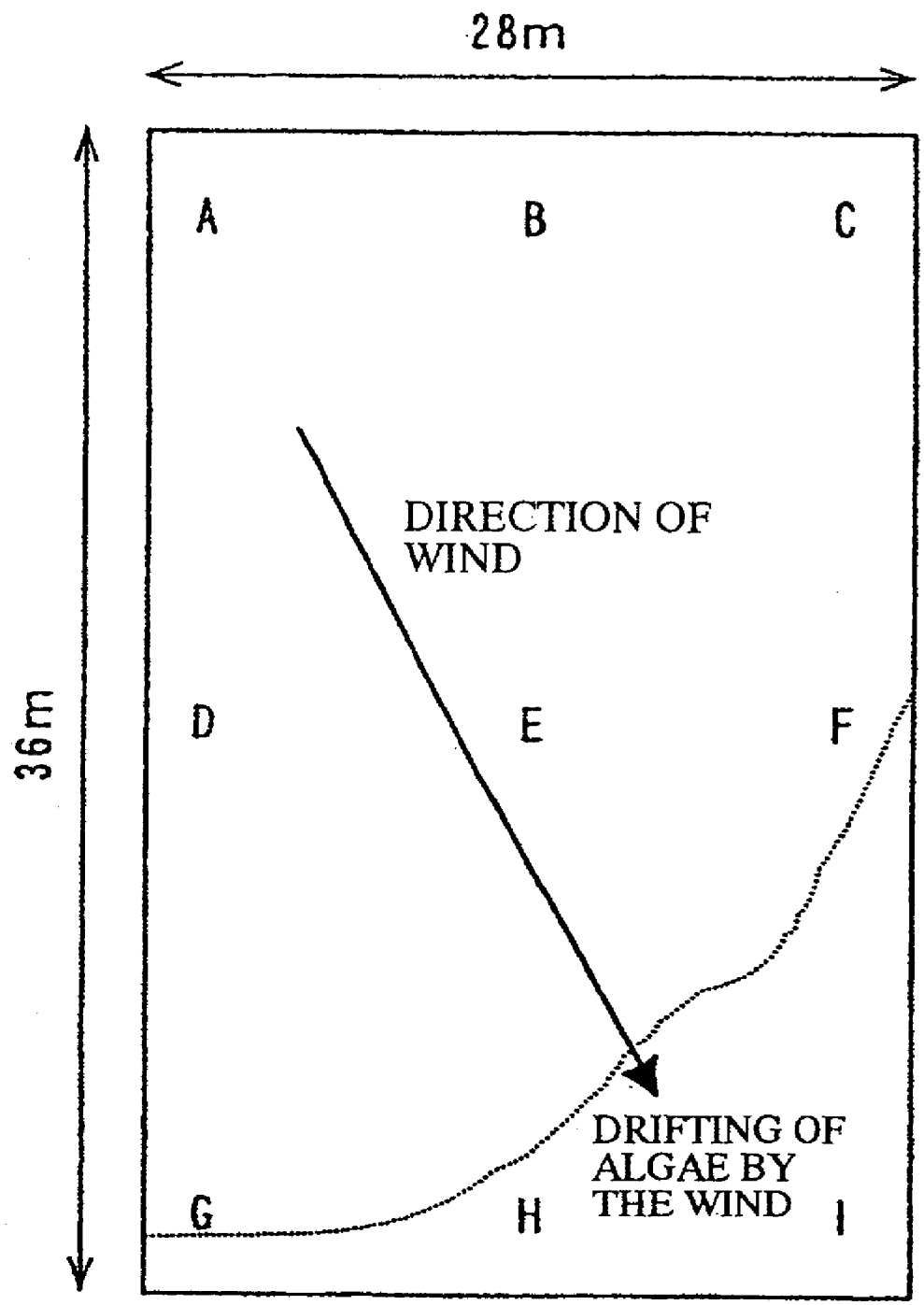
FIG. 1 is a view showing a paddy field used in EXAMPLE 1. In the drawing, a dotted line shows a range where algae are gathered by the wind. Alphabets show sampling points on the paddy field to observe the active ingredient existing at the point on the paddy field in TEST 1.

In the specification of the present invention, "uniform spreadability" designates a state that in spite of scattering (applying) on a partial portion of the area, for instance, a range from about 5% to about 50% of the total area to be applied, the active ingredient substantially spreads uniformly over nearly the total area after a predetermined period of time.

In a uniformly spreadable granular agricultural chemicals formulation (hereinafter referred to as "a spreadable granular formulation") of the present invention, an agrochemically active ingredient which can be used as a raw material is not limited in particular provided that it is used generally as an agricultural chemicals, and any solid or liquid agricultural chemicals can be used. Furthermore, the agrochemically active ingredient may be hardly soluble or easily soluble in water. For instance, herbicides, fungicides, insecticides, and plant growth regulators can be used, and among them, an agrochemically active ingredients useful for applying on water surface is preferable.

As examples of an agrochemically active ingredient used in the present invention, herbicides, fungicides, insecticides, and plant growth regulators are cited, but it is not limited to these substances.

Among these agrochemically active ingredients, concrete examples of the herbicide are, for instance, 2,4,6,-trichlorphenyl-4-nitrophenylether(CNP), 2-methyl-4-chlorophenoxy-thioacetic acid-s-ethyl(phenothiol), α-(2-naphthoxy)propionanilide(naproanilide), 5-(2,4-dichlorophenoxy)-2-nitrobenzoatemethyl(bifenox), S-(4-chlorbenzyl)N,N-diethylthiocarbamate(benthiocarb), S-benzyl-1,2-dimethlpropyl(ethyl)thiocarbamate(esprocarb), S-ethylhexahydro-1H-azepin-1-carbothioate(molinate), S-1-methyl-1-phenylethyl-piperidine-1-carbothioate(dimepiperate), O-3-tert-butylphenyl-6-methoxy-2-pyridyl(methyl)thiocarbamate(pyributicarb), 2-chloro-2',6'-diethyl-N-(butoxymethyl)acetanilide(butachlor), 2-chloro-2',6'-diethyl-N-(2-propoxyethyl)acetanilide(pretilachlor), (RS)-2-bromo-N-(α,α-dimethylbenzyl)-3,3-dimethylbutylamide (bromobuthyde), 2-benzothiazol-2-yloxy-N-methylacetanilide(mefenacet), 1-(α,α-dimethylbenzyl)-3-(paratryl)urea(dimron), methyl-α-(4,6-dimethoxypyrimidine-2-ylcarbamoylsulfamoyl)-O-toluate (bensulfuron-methyl), 1-(2-cloroimidazo[1,2-a]pyridine-3-ylsulfonyl)-3-(4,6-dimethoxypyrimidine-2-yl)urea (imazosulflon), ethyl-5-(4,6-dimethoxypyrimidine-2-ylcarbamoylsulfamoyl)-1-methylpyrasol-4-carboxylate (pyrazosulfuron-ethyl), 2-methythio-4,6-bis(ethylamino)-s-triazine(simetryne), 2-methylthio-4,6-bis(isopropylamino)-s-triazine(prometryn), 2-methylthio-4-ethylamino-6-(1,2-dimethylpropylamino)-s-triadine(dimethametryn), 2,4-dichlorophenyl-3'-methoxy-4'-nitrophenylether (chlomethoxynil), 5-tert-butyl-3-(2,4-dichoro-5-isopropoxyphenl)-1,3,4-oxadiazorin-2-one(oxadiazon), 4-(2,4-dichlorobenzoyl)-1,3-dimethyl-5-pyrazoryl-p-toluensulfonate(pyrazolate), 2-[4-(2,4-dichlorobenzoyl)-1,3-dimethylpyrazole-5-yloxy]acetophenone(pyrazoxyfen), (RS)-2-(2,4-dichloro-m-tolyloxy)propionanilide(clomeprop), 2-[4-[2,4-dichloro-m-toluoyl]-1,3-dimethylpyrazole-5-yloxy]-4'-methylacetophenon(benzofenap), S,S'-dimethyl-2-difluoromethyl-4-isobutyl-6-trifluoromethylpyridine-3,5-dicarbithioate(dithiopyl), 2-chloro-N-(3-methoxy-2-thenyl)-2',6'-dimethylacetanilide (thenylchlor), n-butyl-(R)-2-[4-(2-fluoro-4-cyanophenoxy) phenoxy]propionate(cyhalofop-butyl), 3-[1-(3,5-dichlorphenyl)-1-methylethyl]-2,3-dihydro-6-methyl-5-phenyl-4H-1,3-oxazine-4-one(oxaziclomefone), 3-(4-chloro-5-cyclopentyloxy-2-flyorophenyl)-5-isopropyridene-1,3-oxazolidine-2,4-dione(pentoxazone), 1-(diethylcarbamoyl)-3-(2,4,6-trimethylphenylsulfonyl)-1,2,4-triazole (cafenstrole), N-{[(4,6-dimethoxypyrimidine-2-yl) aminocarbonyl]}-1-methyl-4-(2-methyl-2H-tetrazole-5-yl) (azimsulfuron), methyl 2-[(4,6-dimethoxypyrimidine-2-yl)oxy]-6-[(E)-1-(methoxyimino)ethyl]benzoate(pyriminobacmethyl) and so on.

Concrete examples which can be cited as a fungicide are, O,O-diisopropyl-S-benzylthiophosphate(IBP), 3'-isopropoxy-2-methylbenzanilide(mepronil), α,α,α-trifluoro-3'-isopropoxy-O-toluanilide(flutolanil), 3,4,5,6-tetrachloro-N-(2,3-dichlorophenyl)phthalamid acid(tecloftalam), 1-(4-chlorobenzyl)-1-cyclopentyl-3-phenylurea(pencyclon), 6-(3,5-dichloro-4-methylphenyl)-3(2H)-pyridazinone(diclomezin), methyl-N-(2-methoxyacetyl)-N-(2,6-xylyl)-DL-alaninate(metalaxyl), (E)-4-chloro-α,α,α-trifluoro-N-(1- imidazole-1-yl-2-propoxyethylidene)-o-toluidine (triflumizole), kasugamycin, baridamicine, 3-aryloxy-1,2-benzoisothiazole-1,1-dioxyd(probenazole), diisopropyl-1,3-dithiolan-2-ylidene-malonate(isoprothiolane), 5-methyl-1,2,4-triazoro [3,4-b]benzothiazole(tricyclazole), 1,2,5,6-tetrahydropylolo[3,2,1-ij]chinoline-4-one(pyroquilon), 5-ethyl-5,8-dihydro-8-oxo [1,3]dioxolo[4,5-g]chinoline-7-carboxylic acid(oxolinic acid), (Z)-2'-methylacetophenone-4,6-dimethylpyrimidin-2-ylhydrazone 4,5,6,7-tetrachlorophthalide(ferimzone), 3-(3,5-dichlorophenyl)-N-isopropyl-2,4-ioxoimidazolidine-1-carboxyamide (iprodione) and so on.

Concrete examples which can be cited as an insecticide are O,O-dimethyl-O-(3-methyl-4-nitrophenyl)thiophosphate(MEP), (2-isopropyl-4-methylpyrimidyl-6)-diethylthiophosphate(diazinon), 1-naphthyl-N-methylcarbamate (NAC), O,O-diethyl-O-(3-oxo-2-phenyl-2H-pyridadine-6-yl)phosphorothioate(pyridaphenthion), O,O-dimethyl-O-3,5,6-trichloro-2-pyridylphosphorothioate(chlorpyrifos-methyl), dimethyldicarbethoxyethyldithiophosphate (malathion), O,O-dimethyl-S-(N-methylcarbamoylmethyl) dithiophosphate(dimethoate), O,O-dipropyl-O-4-methylthiophenylphosphate(propaphos), O,S-dimethyl-N-acetylphosphoroamidethioate(acephate), ethylparanitrophenylthiono benzene phosphonate(EPN), 2-secondary-butylphenyl-N-methylcarbamate(BPMC), 2,3-dihydro-2,2-dimethyl-7-benzo[b]flanyl-N-dibutylaminothio-N-methylcarbamate(carbosulfan), ethyl-N-[2,3-dihydro-2,2-dimethylbenzoflan-7-yloxycarbonyl(methyl) aminothio]-N-isopropyl-β-alanynate(benfuracarb), (RS)-α-cyano-3-phenoxybenzyl-(RS)-2,2-dichloro-1-(4-ethoxyphenyl)cyclopropanecarboxylate(cycloprothrin), 2-(4-ethoxyphenyl)-2-methylpropyl-3-phenoxybenzyl-ether (etofenprox), 1,3-bis(carbamoylthio)-2-(N,N-dimethylamino)propanehydrochloride(cartap), 5-dimethylamino-1,2,3-trithian oxalate(thiocyclam), S,S'-2-dimethylamino trimethylene-di(benzenthiosulfonate)(bensultap), 2-tert-butylimino-3-isopropyl-5-phenyl-1,3,5,6 tetrahydro-2H-1,3,5-thiadiazine-4-one(buprofezin), and so on, and concrete examples which can be cited as a PGR (plant growth regulator) are 4'-chloro-2'-(α-hydroxybenzyl)isonicotinanilide(inabenfide), (2RS, 3RS)-1-(4-chlorophenyl)-4,4-dimethyl-2-(1H-1,2,4-triazole-1-yl)pentane-3-ol(paclobutrazol), (E)-(S)-1-(4-chlorophenyl)-4,4-dimethyl-2-(1H-1,2,4-triazole-1-yl)penta-1-ene-3-ol(uniconazole) and so on.

The agrochemically active ingredients described above can be used alone or as a mixture of two kinds or more. The total amount of the agrochemically active ingredients in the formulation is generally in the range from about 0.1 parts by weight to about 70 parts by weight, preferably in the range from about 1 part by weight to about 50 parts by weight, more preferably in the range from 2 parts by weight to 25 parts by weight for 100 parts by weight of the composition.

In a spreadable granular formulation of the present invention, in order to allow the granule to break down on the water surface within 30 minutes and to allow the agrochemically active ingredient to spread into water, a surfactant is preferably contained. As the surfactant which can be used, any surfactant generally used for an agricultural chemicals formulation can be used.

Concrete examples which can be cited as a surfactant are, nonionic surfactants such as polyethylene glycol higher fatty acid ester, polyoxyethylene alkylether, polyoxyethylene alkylarylether, polyoxyethylene arylphenylether, sorbitanmonoalkylate, acetylene alcohol, acetylene diol, and alkylene oxide additives thereof and so on; anionic surfactants such as alkylaryl sulfonate, dialkyl sulfonate, lignin sulfonate, naphthalene sulfonate and its condensate, alkyl sulfate ester, alkyl phosphate ester, alkylarylsulfate ester, alkylaryl phosphate ester, polyoxyethylene alkylether sulfate ester, polyoxyethylene alkylarylether sulfate ester, polyoxyethylene arylphenylether sulfate ester, polycarboxylic acid type polymer surfactant and so on; and further silicone series surfactants or fluorine series surfactants. Incidentally, a liquid surfactant can be used by adsorbing to a solid carrier such as white carbon, diatmite, urea, and the like. These surfactants can be used alone or as a mixture of two kinds or more.

The rate of these surfactants to be used in the formulation is generally from 0.1 parts by weight to 30 parts by weight, preferably from 0.5 parts by weight to 20 parts by weight, more preferably from 2 parts by weight to 10 parts by weight for 100 parts by weight of the agricultural chemicals composition.

It is absolutely necessary for the spreadable granular formulation of the present invention to be floatable on the water surface. As a method for imparting water-floatability to the spreadable granular formulation, a method of containing a floatable carrier having an independent single or plural air chambers such as pearlite derived from pearlstone or obsidian, foamed shirasu derived from shirasu, filite obtained by calcination of aluminosilicates, microbaloon which is made by foaming sodium silicate or borax, pumice, granular diatmite, granular activated carbon, wood powder, cork powder, kenaf pieces, phenol microbaloon made from phenol resin, echo-sphere made from epoxy resin, polyurethane foam made from polyurethane, microsphere made from polyacrylonitrile, fly ash obtained as a by-product when performing thermal power generation, and so on, and a method of containing a water repellant substance such as stearic acid and the salts thereof, hydrophobic white carbon and so on, can be cited. Between them, a method of containing a floatable carrier having an independent single or plural air chambers as described in the former is preferable.

The amount of the floatable carrier or water repellant substance in the formulation is not limited per se provided that it is sufficient to allow the spreadable granular formulation to float on water. When this floatable carrier or water repellant substance is present in excess, the granular formulation becomes fragile which leads to premature breakdown and the generation of a large amount of dust during application, which is undesirable. Accordingly, it is preferable to formulate the minimum amount required. Therefore, the upper limit of content of the floatable carrier and the like is generally about 30 parts by weight at the maximum, normally about less than 20 parts by weight, preferably less than 15 parts by weight for 100 parts by weight of the formulation. The lower limit is 0.3 parts by weight, and it is preferable to be 0.5 parts by weight or more.

In the spreadable granular formulation of the present invention, it is desirable that some water is present in the formulation in order to enhance the effect of above-described floatable carrier. The amount of water added in the formulation is about 0.3 to about 6 parts by weight, desirably about 0.5 parts by weight to about 5 parts by weight, and more preferably about 0.8 parts by weight to about 3 parts by weight for 100 parts by weight of the formulation. When water content is less than 0.3 parts by weight, it takes a structure such that water may easily penetrate into the formulation. Accordingly, when the formulation is scattered over water, it first floats on the surface, later air in the formulation comes out causing the formulation to settle. In order to prevent settlement, more than the required amount of the above-described floatable carrier must be present, which is not favorable. When water content is more than 6 parts by weight, it is also not favorable because the formulation becomes fragile and often generates dust when it is applied.

As a method for including water in the spreadable granular formulation of the present invention, a method of adding water by spraying after first drying the formulation completely, or a method of drying the formulation while measuring the water content and stopping drying when a predetermined water content is obtained can be cited, but it is not limited to this method. Incidentally, the water content in the spreadable granular formulation of the present invention can be measured by equipment such as a Karl Fischer's moisture meter, an infrared moisture meter or the like.

In addition, in the present invention, a solid carrier is generally formulated. As a solid carrier, water-soluble carrier or water-insoluble carrier can be used and a mixture thereof can be also used. Examples which can be used as a water-soluble carrier are: for instance, organic or inorganic salt such as ammonium sulfate, ammonium bicarbonate, ammonium nitrate, ammonium chloride, potassium chloride, sodium sulfate, magnesium sulfate, sodium citrate, sodium carbonate, sodium hydrogen carbonate, and so on; organic acid such as citric acid, succinic acid, and so on, sugar such as cane sugar, lactose, and so on; and urea and so on. Further, as a water-insoluble carrier, a mineral fine powder is generally used, and, for instance, clay family, calcium carbonate, bentonite, talc, diatomite, calcium stearate, white carbon, and so on can be cited. The amount of these solid carriers in the formulation is generally 5 parts by weight to 80 parts by weight, preferably 10 parts by weight to 70 parts by weight for 100 parts by weight of the composition.

In the present invention, an adjuvant is formulated when necessary as other components. As an example of an adjuvant which is an optional component, a binder and organic solvent can be cited. The binder which can be used is what is generally used in an agricultural chemicals of granular composition. A water-soluble substance is preferable. Examples of binders are, sodium salt of carboxymethycellulose, dextrine, water-soluble starch, xanthan gum, guaseed gum, sugar cane, polyvinylpyrolidone, polyvinylalcohol, sodium polyacrylate, polyethylene glycol having an average molecular weight of 6,000 to 20,000, polyethylene oxide having an average molecular weight of 100,000 to 5000,000, and so on. The amount in the formulation for these binders are generally 0.01 parts by weight to 10 parts by weight, preferably 0.1 parts by weight to 6 parts by weight for 100 parts by weight of the composition.

Still further, when the agrochemically active ingredient is dissolved or dispersed, organic solvent is used. Examples of organic solvents are, dioctyl phthalate, methyl naphthalene, alkylpyrolidone, phenylxylyl ethane, glycerin, alkylene glycol, machine oil, methane series hydrocarbons, fatty acid ester, polybasic acid, coconut oil, bean oil, rapeseed oil, silicone oil, and so on. Among them, solvent having a high boiling point is preferable. The amount of the organic solvent in the formulation is generally 10 parts by weight to 200 parts by weight for the agrochemically active ingredient.

The spreadable granular formulation of the present invention is generally a granular formulation which floats on the surface of paddy water, containing the above-explained components, and when a formulation having a particle diameter of 3 mm or more is prepared, each of the above components and the amount in the formulation are adjusted so that the formulation breaks down on the water surface within 30 minutes. If time required for the breakdown is more than 30 minutes, it is not favorable because the formulation may be drifted by the wind. In order to make the effect of drifting small, it is desirable to adjust the amount of each component described above in a manner that the exposed portion above the water surface is 40% or less, preferably 20% or less of the entire formulation when the formulation floats on the water surface.

Though a method for manufacturing the spreadable granular formulation of the present invention which satisfies the above conditions is not limited to a specific method, it is preferable to granulate the composition by extruding a kneaded composition from a plate with a hole having a predetermined size after mixing all the materials except water, and then kneading with water. The extruded product is cut into suitable lengths, and rolled to produce granules. The composition is shaped by stopping the rolling when the surface of the granule becomes smooth. The size of the granular substance at this time is preferably 1 to 3 with respect to the ratio of breadth to length of one granule. In order to obtain a uniformly spreadable granular agricultural chemicals formulation, the shaped granule may be dried to have water content of 0.3 parts by weight to 6 parts by weight for 100 parts by weight of the formulation, or water may added by spraying after completely drying the shaped granule in a manner that moisture content becomes 0.3 parts by weight to 6 parts by weight of moisture for 100 parts by weight of the formulation.

As a preferred example of the spreadable granular formulation of the present invention, a granule containing an active ingredient effective for application on the surface of paddy water, having an average particle diameter from 4 mm to 10 mm, and specific gravity of 1 or less, and property of breaking down within 1 minute to 20 minutes after scattering (applying) on the water surface can be cited.

As described above, it is absolutely necessary for the spreadable granular formulation of the present invention to have a particle diameter of 3 mm or more, and it is preferable to include more particles having particle diameter of about 3 mm to about 20 mm, especially about 4 mm to about 10 mm. By making the particle diameter to be the above-described diameter, even when the spreadable granular formulation of the present invention is scattered (applied) from a levee, the area of application corresponding to 5% to 50% of the total area of the paddy field can be easily obtained at a distance of 1 m or more from the levee. In addition, as a secondary effect of making the particle diameter to be 3 mm or more, it is possible that misuse can be prevented because the product can be easily distinguished from granular formulation applied to nursery boxes which generally have a particle diameter of 0.8 mm or so. If the spreadable granular formulation is applied to a nursery box by mistake and misuse is found thereafter, damage caused by the misuse can be minimized because only the formulation of the present invention comes up to the water surface when the nursery box and others are immersed together in water.

As a method to scatter (apply) the above-explained spreadable granular formulation of the present invention onto the surface of water of a paddy field or the like, it is not limited to specific method, and a method of throwing the formulation with a hand covered with a vinyl globe, a method of scattering (applying) the formulation by discharging it from a blow head continuously using a power applicator, a method of scattering (applying) the formulation by discharging it intermittently by opening and closing a shutter lever instantaneously, a method of throwing the formulation with a ladle, a method of throwing the formulation by shaking a cylindrical vessel, a method of applying with a hand granule applicator, or a method of scattering (applying) the formulation in a stripe-like or in a spot-like using a radio-controlled helicopter are cited.

In rice farming on a paddy field, in a case of so-called early plantation, that is, the time of transplantation is rather early, even if the water-floatable agricultural chemicals are applied locally within a period of 1 to 2 weeks after transplantation, there generates little algae in the paddy field, and the spreadability of the agrochemically active ingredient is excellent so that the expected effect can be obtained. However, in so-called normal plantation in which the season of transplantation is after May, water temperature rises and usually algae generate during the best season for applying the agricultural chemicals. The algae considerably disturb the spreading of the agrochemically active ingredient, which often makes it difficult to obtain the desired effect of the agricultural chemicals. Especially, when the water-floatable agricultural chemicals formulation is scattered (applied) locally on a paddy field in which algae are gathered by the wind, it is the actual circumstances that the effect of the agricultural chemicals can not be obtained on the portion where the algae are gathered by the wind. In a case of scattering (applying) a water-floatable agricultural chemicals formulation locally after several weeks of the transplantation when the paddy rice grow on and roots of the rice become big, spreading of the agrochemically active ingredient is also disturbed. Thus, the formulation for labor-saving application under the assumption of local application is conventionally a formulation to be applied when roots of rice are still small.

On the other hand, the spreadable granular formulation of the present invention is a water-floatable granular agricultural chemicals formulation which is excellent in spreadability of an agrochemically active ingredient and from which the desired effect of the agricultural chemicals can be obtained in a paddy field where algae are growing, or even in a paddy field where roots of rice grow to some extent. By scattering (applying) the present spreadable granular agricultural chemicals formulation in specific positions and in specific areas in a paddy field, uniform scattering (applying) of the agrochemically active ingredient can be achieved practically without damaging its labor-saving property when applying the agricultural chemicals. That is, the spreadable granular formulation of the present invention having particles of 3 mm or more in particle diameter in the rate of 80% or more, floats on the surface of paddy water and breaks down on the surface of the paddy water within 30 minutes, can apply its agrochemically active ingredient uniformly in a paddy field when scattered (applied) on 5% to 50%, preferably 10% to 50% of the total area of the paddy field from the levee of a submerged paddy field at a distance of 1 m or more, preferably 2 m or more.

There presents no problem when the spreadable granular formulation of the present invention is applied on more than 50% of the total area of a paddy field, however, it is no use from the point of labor-saving application of agricultural chemicals, so it is preferable to scatter (apply) on 50% or less of a paddy field. In Japanese Patent Laid-open No. Hei 7-233002, there is a description that a water-floatable granular formulation having a particle diameter from 1 mm to 5 mm could be thrown from a levee of a paddy field. This description is not concrete, and does not describe anything about whether it can obtain the uniform spreadability as in the present invention. Furthermore, as a matter of course, an excellent spreadability of an agrochemically active ingredient can be obtained with the spreadable granular formulation of the present invention in a paddy field without growth of algae, in a paddy field before transplantation, and in a paddy field where rice plants are still young, so that the desired effect of the agricultural chemicals can be obtained.

EXAMPLE

The present invention will be explained in detail hereinafter referring to examples and test examples, but the present invention is not limited to these examples. Incidentally, a term "parts" indicates "parts by weight" in the following examples.

Formulation Example 1

1.2 parts of pyriminobac-methyl, 2.1 parts of bensulfuron-methyl, 9 parts of mefenacet and 4 parts of polyoxyethylene arylphenylether surfactant are adsorbed to 4 parts of white carbon to prepare powders. After mixing uniformly this powder, a powder made of 2.5 parts of acetylene alcohol surfactant adsorbed to 2.5 parts of white carbon, 1 part of polyvinyl alcohol, 10 parts of potassium chloride and 62 parts of anhydrous Grauber's salt, the mixture is pulverized with an impact crusher.

The powder obtained thus and 1 part of microsphere are mixed uniformly in a high speed stirring mill, and after kneading with an appropriate amount of water, extruding granulation is performed with a plate having a hole of 5 mm in diameter. Then, the extruded product is cut into pieces of 10 mm in length. This product is put in a drum which is laid horizontally, and is given a rolling movement through rotation of the drum to obtain a round-shaped product. The round-shaped product is dried until the moisture content comes to 0.7 parts by weight to obtain a granular agricultural chemicals formulation having water-floatability. The particle-size distribution of the granular agricultural chemicals formulation is such that 85% or more of the particles present have an average particle diameter of 3 mm or more. When 100 granules of the present formulation are thrown in a vessel filled with water, all granules float on the water surface. Incidentally, the breakdown time of the granules during floating is 10 minutes.

Formulation Example 2

1.5 parts of bensulfuron-methyl, 20 parts of mefenacet, and 3 parts of polyoxyethylene arylphenylether surfactant are adsorbed to 3 parts of white carbon to prepare powders. After mixing uniformly this powder, a powder made of 3 parts of polyoxyethylene arylphenylether phosphate ester surfactant adsorbed to 3 parts of white carbon, a powder made of 3 parts of acetylene alcohol surfactant absorbed to 3 parts of white carbon, 2 parts of dextrine, and 37.5 parts of potassium chloride, the mixture is pulverized with an impact crusher.

The powder obtained thus and 18 parts of foamed shirasu are mixed uniformly in a high speed stirring mill, and after kneading with an appropriate amount of water, extruding granulation is performed with a plate having a hole of 3 mm in diameter. Then, the extruded product is cut into pieces of 10 mm in length. This product is put in a drum which is laid horizontally, and is given a rolling movement through rotation of the drum to obtain a round-shaped product. The round-shaped product is dried until the moisture content comes to 3 parts by weight to obtain a granular agricultural chemicals formulation having water-floatability. The particle-size distribution of the granular agricultural chemicals formulation is such that 100% of the particles present have an average particle diameter of 3 mm or more. When 100 granules of the present formulation are thrown in a vessel filled with water, all granules float on the water surface. Incidentally, the breakdown time of the granules during floating is 7 minutes.

Formulation Example 3

After mixing uniformly a powder prepared by adsorbing 24 parts of bromobuthyde, 8 parts of pentoxazone, 8 parts of alkylnaphthalene formalin condensation salt and 3 parts of dialkylsulfosuccinate to 3 parts of white carbon, a powder prepared by adsorbing 3 parts of acetylene alcohol surfactant to 3 parts of white carbon, 2 parts of dextrin, and 25 parts of urea, the mixture is pulverized with an impact crusher. The powder obtained thus and 18 parts of fly ash baloon are mixed uniformly in a high speed stirring mill, and after kneading with an appropriate amount of water, extruding granulation is performed with a plate having a hole of 3 mm in diameter. Then, the extruded product is cut into pieces of 8 mm in length.

This product is put in a drum which is laid horizontally, and is given a rolling movement through rotation of the drum to obtain a round-shaped product. The round-shaped product is dried at 65° C. at the entrance of a drier until the moisture content comes to 3 parts by weight to obtain a granular agricultural chemicals formulation having water-floatability. The particle-size distribution of the granular agricultural chemicals formulation is such that 85% or more of the particles present have an average particle diameter of 3 mm or more. When 100 granules of the present formulation are thrown in a vessel filled with water, only one cracked granule is settled. Incidentally, the breakdown time of the granules during floating is 8 minutes.

Formulation Example 4

After mixing uniformly a powder prepared by adsorbing 48 parts of pyroquilon, 2.5 parts of polyoxyethylene arylphenylether to 2.5 parts of white carbon, a powder prepared by adsorbing 2.5 parts of acetylene alcohol to 2.5 parts of white carbon, 1.5 parts of enzyme denatured dextrin, and 8 parts of potassium chloride, and 30 parts of anhydrous sodium sulfate, the mixture is pulverized with an impact crusher. The powder obtained thus and 10 parts of hydrous maicrosphere (1 part as the component) are mixed uniformly in a high speed stirring mill, and after kneading with an appropriate amount of water, extruding granulation is performed with a plate having a hole of 5 mm in diameter. Then, the extruded product is cut into pieces of 10 mm in length.

This product is put in a drum which is laid horizontally, and is given a rolling movement through rotation of the drum to obtain a round-shaped product. The round-shaped product is dried at 65° C. at the entrance of a drier until the moisture content comes to 1.5 parts by weight to obtain a granular agricultural formulation having water-floatability. The particle-size distribution of the granular agricultural formulation is such that particles having an average particle diameter of 3 mm or more is 95% or more. When 100 granules of the present formulation are thrown in a vessel filled with water, all granules float on the water surface. Incidentally, the breakdown time of the granules after floating is 6 minutes.

Formulation Example 5

After mixing uniformly a powder prepared by adsorbing 24 parts of mepronil, 8 parts of alkylnaphthalene formalin condensation salt and 3 parts of dialkylsulfosuccinate to 3 parts of white carbon, a powder prepared by adsorbing 3 parts of acetylene alcohol surfactant to 3 parts of white carbon, 2 parts of dextrin, and 31 parts of granular urea, the mixture is pulverized with an impact crusher. The powder obtained thus and 20 parts of foamed shirasu are mixed uniformly in a high speed stirring mill, and after kneading with an appropriate amount of water, extruding granulation is performed with a plate having a hole of 3 mm in diameter. Then, the extruded product is cut into pieces of 8 mm in length.

This product is put in a drum which is laid horizontally, and is given a rolling movement through rotation of the drum to obtain a round-shaped product. The round-shaped product is dried at 65° C. at the entrance of a drier until the moisture content comes to 5.5 parts parts by weight to obtain a granular agricultural formulation having water-floatability. The particle-size distribution of the granular agricultural formulation is such that 85% or more of the particles present have an average particle diameter of 3 mm or more. When 100 granules of the present formulation are thrown in a vessel filled with water, only one cracked granule is settled and other granules float on the water surface. Incidentally, the breakdown time of the granules during floating is 27 minutes.

Formulation Example 6

After mixing uniformly a powder prepared by adsorbing a mixed solution obtained by heating 8 parts of etofenprox, and 4 parts of polyoxyethylene arylphenylether to 12 parts of white carbon, a powder prepared by adsorbing 2.5 parts of acetylene alcohol to 2.5 parts of white carbon, 1 part of polyvinyl alcohol, 10 parts of potassium chloride, and 57 parts of anhydrous sodium sulfate, the mixture is pulverized with an impact crusher. The powder obtained thus and 15 parts of hydrous maicrosphere (1.5 parts as the component) are mixed uniformly in a high speed stirring mill, and after kneading with an appropriate amount of water, extruding granulation is performed with a plate having a hole of 5 mm in diameter. Then, the extruded product is cut into pieces of 10 mm in length.

This product is put in a drum which is laid horizontally, and is given a rolling movement through rotation of the drum to obtain a round-shaped product. The round-shaped product is dried at 65° C. at the entrance of a drier until the moisture content comes to 1.5 parts by weight to obtain a granular agricultural chemicals formulation having water-floatability. The particle-size distribution of the granular agricultural chemicals formulation is such that 95% of the particles present have an average particle diameter of 3 mm or more. When 100 granules of the present formulation are thrown in a vessel filled with water, all granules float on the water surface. Incidentally, the breakdown time of the granules during floating is 12 minutes.

Formulation Example 7

After mixing uniformly a powder prepared by adsorbing 24 parts of cartap hydrochloride, 8 parts of alkylnaphthalene formalin condensation salt and 3 parts of dialkylsulfosuccinate to 3 parts of white carbon, a powder prepared by adsorbing 3 parts of acetylene alcohol surfactant to 3 parts of white carbon, 2 parts of dextrin, and 31 parts of urea, the mixture is pulverized with an impact crusher. The powder obtained thus and 20 parts of shirasu are mixed uniformly in a high speed stirring mill, and after kneading with an appropriate amount of water, extruding granulation is performed with a plate having a hole of 3 mm in diameter. Then, the extruded product is cut into pieces of 8 mm in length.

This product is put in a drum which is laid horizontally, and is given a rolling movement through rotation of the drum to obtain a round-shaped product. The round-shaped product is dried at 65° C. at the entrance of a drier until the moisture content comes to 3 parts by weight to obtain a granular agricultural chemicals formulation having water-floatability. The particle-size distribution of the granular agricultural chemicals formulation is such that 85% or more of the particles present have an average particle diameter of 3 mm or more. When 100 granules of the present formulation are thrown in a vessel filled with water, only one cracked granule is settled and other granules float on the water surface. Incidentally, the breakdown time of the granules during floating is 30 seconds.

Formulation Example 8

After mixing uniformly a powder prepared by adsorbing 24 parts of cartap hydrochloride, 8 parts of alkylnaphthalene formalin condensation salt and 3 parts of dialkylsulfosuccinate to 3 parts of white carbon, a powder prepared by adsorbing 3 parts of acetylene alcohol surfactant to 3 parts of white carbon, 2 parts of dextrin, and 31 parts of urea, the mixture is pulverized with an impact crusher. The powder obtained thus and 20 parts of shirasu are mixed uniformly in a high speed stirring mill, and after kneading with an appropriate amount of water, extruding granulation is performed with a plate having a hole of 7 mm in diameter. Then, the extruded product is cut into pieces of 11 mm in length.

This product is put in a drum which is laid horizontally, and is given a rolling movement through rotation of the drum to obtain a rounded product. The rounded product is dried at 65° C. at the entrance of a drier until the moisture content comes to 3 parts by weight to obtain a granular agricultural formulation having water-floatability. The particle-size distribution of the granular agricultural chemicals formulation is such that 100% of the particles present have an average particle diameter of 3 mm or more. When 100 granules of the present formulation are thrown in a vessel filled with water, only one cracked granule is settled and other granules float on the water surface. Incidentally, the breakdown time of the granules during floating is 15 minutes.

Comparison Formulation Example 1

A granular agricultural chemicals formulation is prepared in the same manner as in the FORMULATION EXAMPLE 1 except it is dried until the moisture content comes to 0.1 parts by weight. When 100 granules of thus-obtained formulation are thrown in a vessel filled with water, about 50 granules are settled without floating. Incidentally, the floated granules do not break down after 30 minutes.

Comparison Formulation Example 2

For the agricultural granular composition in FORMULATION EXAMPLE 1, extruding granulation is performed with a plate having a hole of 1.5 mm in diameter, and the extruded product is cut into pieces of 4.5 mm in length. This product is put in a drum which is laid horizontally, and is given a rolling movement through rotation of the drum to obtain a round-shaped product. Then, it is dried until the moisture content comes to 0.8 parts by weight to obtain the COMPARISON FORMULATION EXAMPLE 2 having water-floatability. The particle-size distribution of the granular agricultural chemicals formulation is such that particles having an average particle diameter of 3 mm or more can not be observed. When 100 granules of the present formulation are thrown in a vessel filled with water, 15 granules are settled and other granules float on the water surface. All floated granules are settled within 30 second and breaks down at the bottom after a while.

Example 1

250 g of the granular agricultural chemicals formulation of the FORMULATION EXAMPLE 1 is divided into groups each having a handful amount of 8.3 g, and scattered (applied) from a levee into 10 are of a submerged paddy field having an average water-depth of 5 cm shown in FIG. 1, one week after transplantation of young rice where algae are growing. At this time, the shortest distance of the scattered area (the shortest distance between the levee from where the granules are scattered and positions where the granules fall when the granules are scattered. The same expression is used hereinafter) is found to be 2 m to 6 m from the levee. Just after the application, the position where the granule falls is confirmed by several persons concerned and marked with a pole. Then, the scattered area is calculated using measurements of distance between poles to find the ratio of the scattered area to the total paddy field. As a result, the ratio of the scattered area is 11.2%.

Example 2

Figure 2:
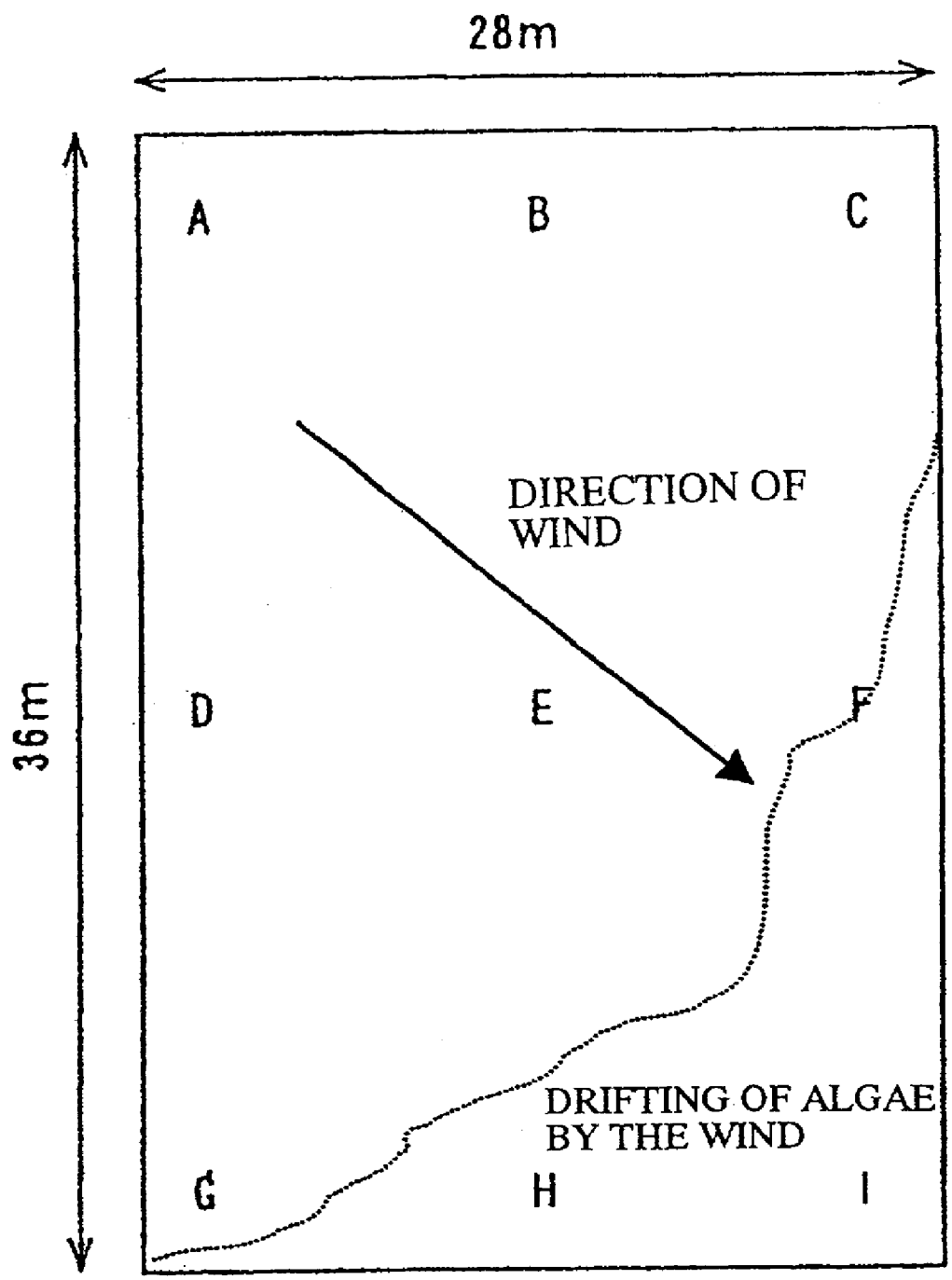
FIG. 2 is a view showing a paddy field used in EXAMPLE 2. In the drawing, a dotted line and alphabets have the same meaning as in FIG. 1.

250 g of the granular agricultural chemicals formulation of the FORMULATION EXAMPLE 1 is scattered at 10 g per one throw from a levee into 10 are of a submerged paddy field having an average water-depth of 5 cm shown in FIG. 2, one week after transplantation of young rice where algae are growing, using a ladle having a handle of 40 cm in length. At this time, the shortest distance of the scattered area is found to be 3 m to 8 m from the levee. Just after the application, the positions where the granules fall are marked with poles. Then, the scattered area is calculated by measuring the distance between poles to find the ratio of the scattered area to the total area of the paddy field. As a result, the ratio of the scattered area is 15.8%.

Example 3

Figure 3:
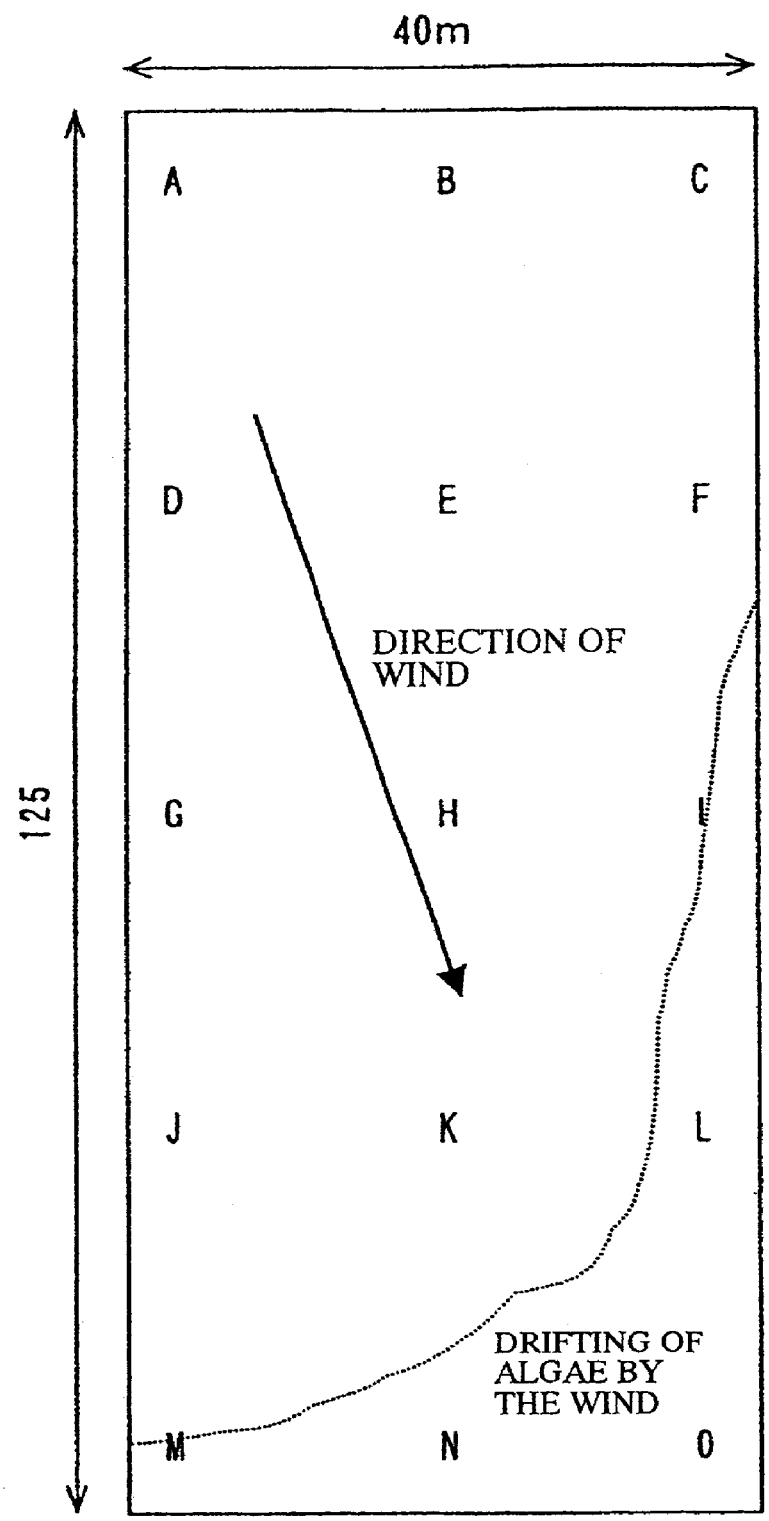
FIG. 3 is a view showing a paddy field used in EXAMPLE 3. In the drawing, a dotted line and alphabets have the same meaning as in FIG. 1.

1250 g of the granular agricultural chemicals formulation of the FORMULATION EXAMPLE 1 is charged into a power applicator equipped with a short blow head only, and scattered by blowing off the formulation intermittently from a levee by means of opening and closing a shutter lever instantaneously into 50 are of a submerged paddy field having an water-depth of 4 cm shown in FIG. 3, one week after transplantation of young rice where algae are growing. At this time, the shortest distance of the scattered area is found to be 10 m to 15 m from the levee, and 1250 g of the formulation is applied in 42 times of throwing. The extent of scattered granules are marked with poles. Then, the scattered area is calculated by measuring the distance between poles to find the ratio of the scattered area to the total area of the paddy field. As a result, the ratio of the scattered area is 29.4%.

Example 4

Figure 4:
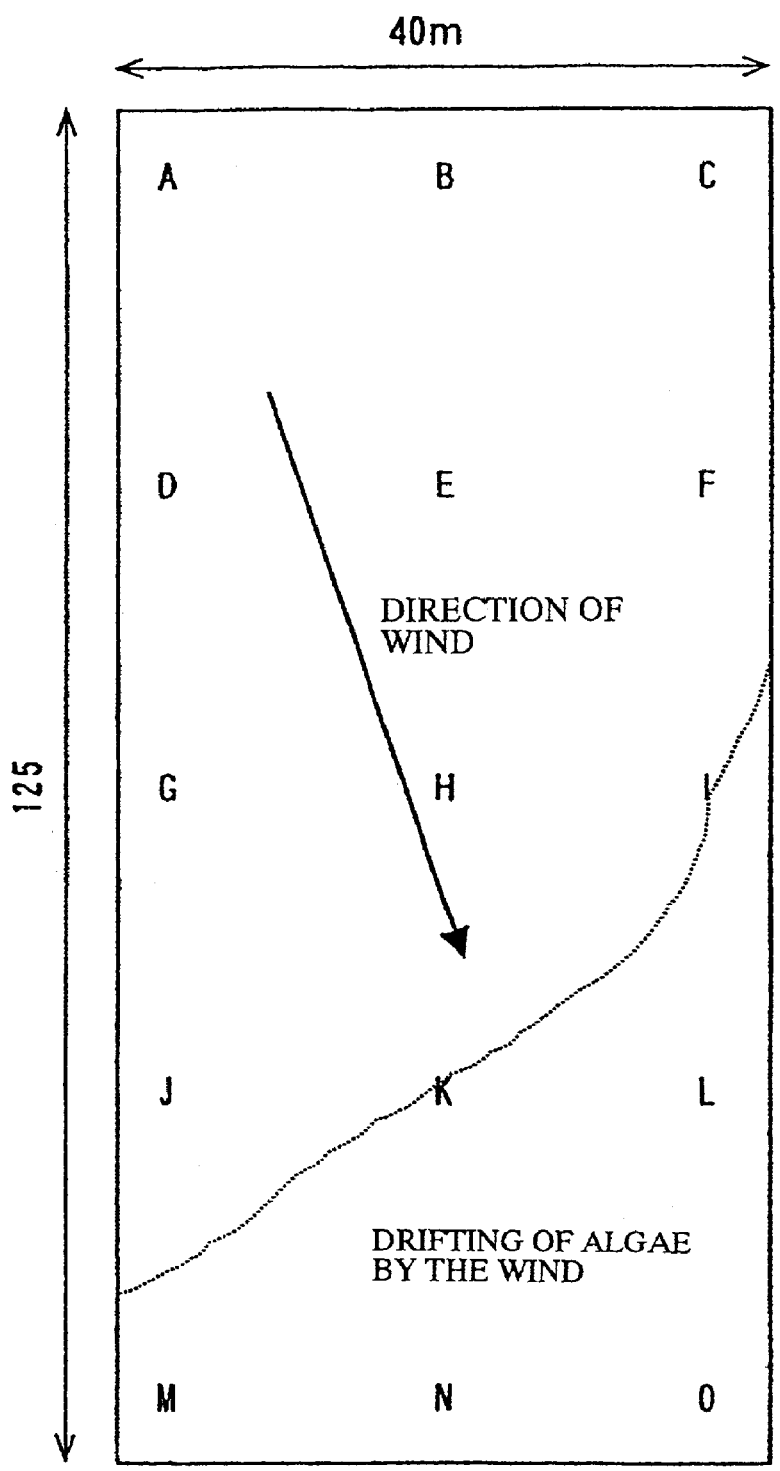
FIG. 4 is a view showing a paddy field used in EXAMPLE 4. In the drawing, a dotted line and alphabets have the same meaning as in FIG. 1.

1250 g of the granular agricultural chemicals formulation of the FORMULATION EXAMPLE 1 is charged into a power applicator equipped with a short blow head only, and scattered continuously while walking along the levee by means of adjusting a shutter lever into 50 are of a submerged paddy field having an average water-depth of 4 cm shown in FIG. 4, one week after transplantation of young rice where algae are growing. At this time, the shortest distance of the scattered area is found to be 10 m, and the longest flying distance is found to be 20 m. The calculated result for the ratio of the scattered area to the total area of the paddy field at this time is found to be 29.0%.

Example 5

Figure 5:
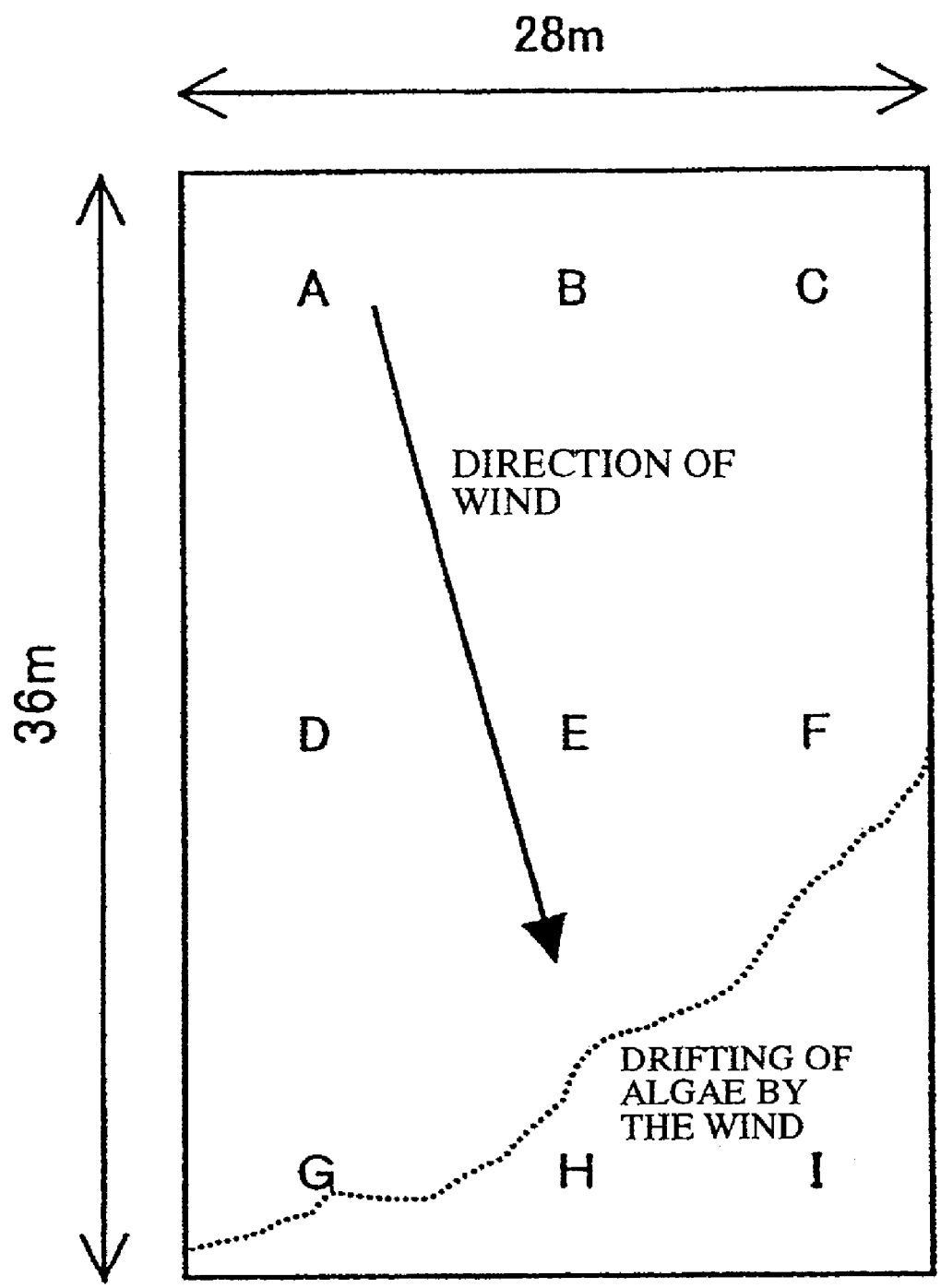
FIG. 5 is a view showing a paddy field used in EXAMPLE 5. In the drawing, a dotted line and alphabets have the same meaning as in FIG. 1.

250 g of the granular agricultural chemicals formulation of the FORMULATION EXAMPLE 6 is scattered while walking around along the levee by the scattering method described in example 4 into 10 are of a submerged paddy field having average water-depth of 5 cm shown in FIG. 5, one week after transplantation of young rice where algae are growing. At this time, the shortest distance of the scattered area is found to be 10 m, and the longest flying distance is found to be 20 m. The calculated result for the ratio of the scattered area to the total area of the paddy field at this time is found to be 47.8%. One week after the application of the granular agricultural chemicals formulation, the degree of damage caused by inemizuzoumushi is checked. As a result, none of the damage is found at all in a district on which the present treatment is applied. In the adjacent district on which no treatment with the agricultural chemicals formulation is applied, about half of rice are found to be damaged by inemizuzoumushi.

Comparison Example 1

Figure 6:
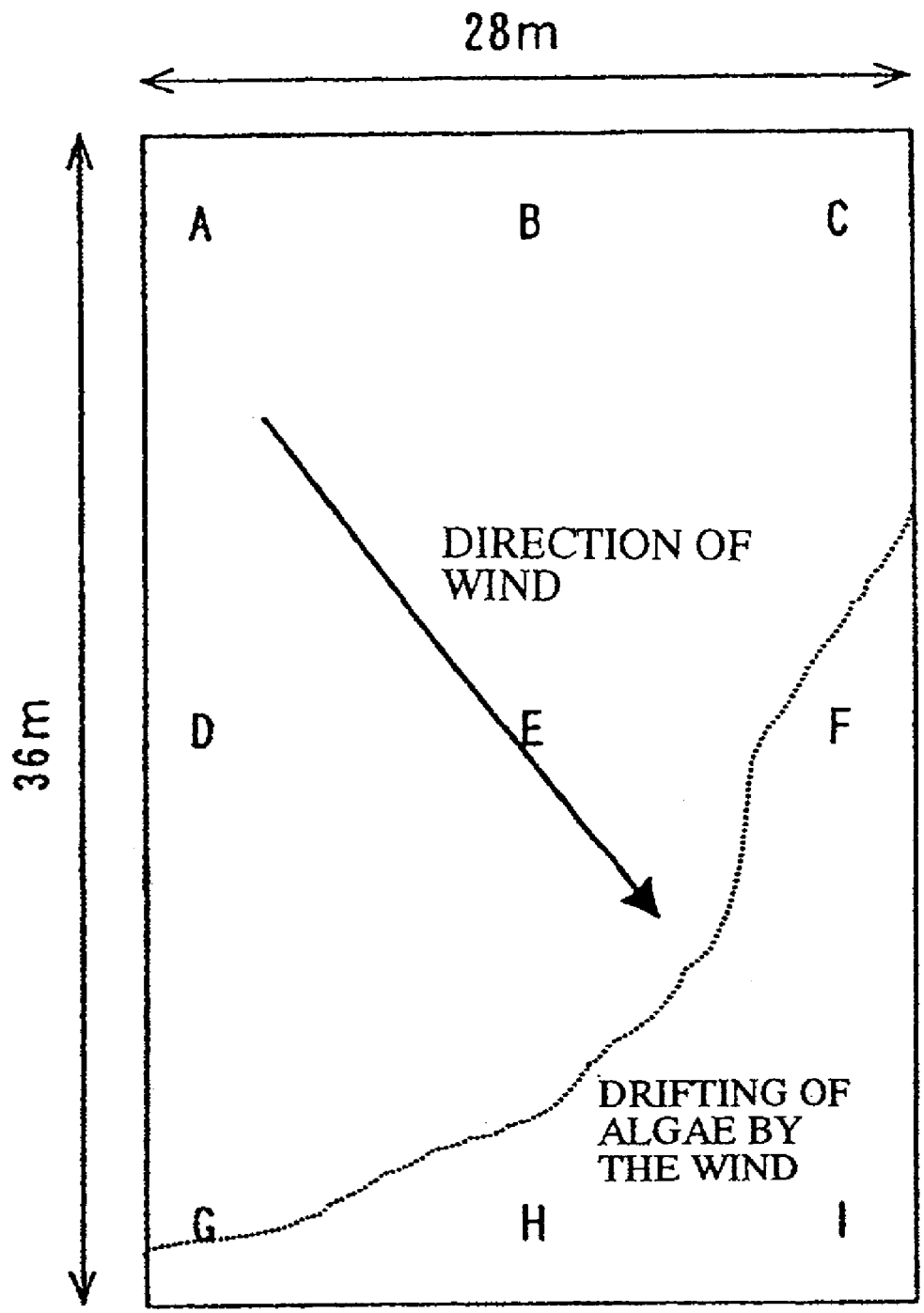
FIG. 6 is a view showing a paddy field used in COMPARISON EXAMPLE 1. In the drawing, a dotted line and alphabets have the same meaning as in FIG. 1.

250 g of the granular agricultural chemicals formulation of the FORMULATION EXAMPLE 1 is put into an aluminum bag and scattered by dropping the agricultural chemicals down on the water surface around the foot while walking along a levee to apply into 10 are of a submerged paddy field having an average water-depth of 5 cm shown in FIG. 6, one week after transplantation of young rice where algae are growing. At this time, the shortest distance of the scattered area is found to be 0.5 m, and the width of the application is found to be 0.3 m. The calculated result for the ratio of the scattered area to the total area of the paddy field at this time is found to be 4.2%.

Comparison Example 2

Figure 7:
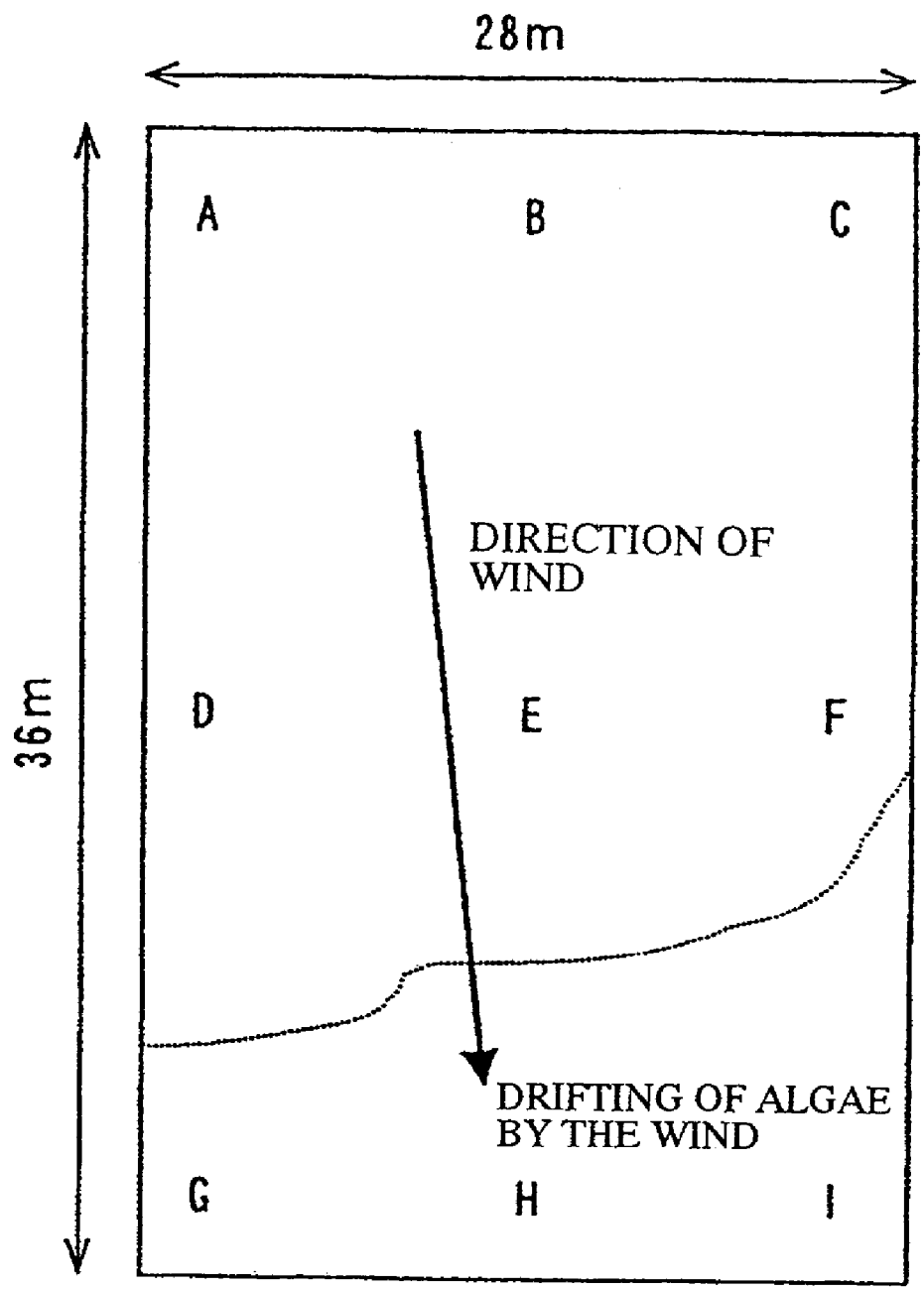
FIG. 7 is a view showing a paddy field used in COMPARISON EXAMPLE 2. In the drawing, a dotted line and alphabets have the same meaning as in FIG. 1.

250 g of the granular agricultural chemicals formulation of the FORMULATION EXAMPLE 1 is scattered at 10 g per one throw with a cup from a levee into 10 are of a submerged paddy field having an average water-depth of 5 cm shown in FIG. 7, one week after transplantation of young rice where algae are growing. At this time, the shortest distance of the scattered area is found to be 2 m to 3 m from the levee. The extent of scattered granules is marked with poles. Then, the scattered area is calculated by measuring the distance between poles to find the ratio of the scattered area to the total area of the paddy field. As a result, the ratio of the scattered area is 3.5%.

Test 1

Water is gathered 24 hours after the application from points shown by alphabets on the paddy field in FIGS. 1 to 4 and FIGS. 6 to 7 and analyzed to find the concentration of the agrochemically active ingredient. The theoretical concentration in water is assumed to be 100% if the agrochemically active ingredient is uniformly dispersed in the water, the ratio of measured concentration to the above theoretical concentration is found, and the coefficient of variation is calculated by dividing a standard deviation of the concentration in water at each point with the average value. The results will be shown in Tables 1, 2 and 3. One month after the application, the effect of herbicide against barnyard grass which is in the 1.5th period in leaf growing (1.5 Leaf Stage) at the time of application is observed for the points shown by alphabets on the paddy field in FIGS. 1 to 4 and FIGS. 6 to 7, and the result is expressed using indexes of 0 (no effect) to 5 (completely dead). The result will be shown in Table 4.

TABLE 1

|  | pyriminobac-methyl | bensulfuron-methyl | mefenacet |
|---|---|---|---|
| Example 1 | | | |
| point A | 90 (%) | 86 (%) | 76 (%) |
| point B | 92 | 91 | 80 |
| point C | 86 | 95 | 71 |
| point D | 91 | 82 | 69 |
| point E | 84 | 90 | 82 |
| point F | 83 | 95 | 85 |
| point G | 90 | 90 | 71 |
| point H | 79 | 84 | 66 |
| point I | 76 | 81 | 62 |
| Average (%) | 85.7 | 88.2 | 73.6 |
| Deviation (%) | 6.6 | 5.9 | 10.5 |
| Example 2 | | | |
| point A | 88 (%) | 90 (%) | 70 (%) |
| point B | 91 | 85 | 73 |
| point C | 87 | 91 | 86 |
| point D | 93 | 80 | 71 |
| point E | 84 | 79 | 79 |
| point F | 90 | 93 | 85 |
| point G | 86 | 83 | 80 |
| point H | 79 | 77 | 67 |
| point I | 83 | 72 | 62 |
| Average (%) | 86.8 | 83.3 | 74.8 |
| Deviation (%) | 5.0 | 8.5 | 11.0 |

TABLE 2

|  | pyriminobac-methyl | bensulfuron-methyl | mefenacet |
|---|---|---|---|
| Example 3 | | | |
| point A | 85 (%) | 91 (%) | 70 (%) |
| point B | 91 | 90 | 75 |
| point C | 80 | 82 | 81 |
| point D | 83 | 96 | 69 |
| point E | 91 | 94 | 85 |
| point F | 81 | 86 | 71 |
| point G | 77 | 91 | 81 |
| point H | 73 | 77 | 76 |
| point I | 82 | 85 | 77 |
| point J | 77 | 83 | 80 |
| point K | 71 | 81 | 81 |
| point L | 70 | 71 | 73 |
| point M | 91 | 89 | 69 |
| point N | 71 | 68 | 61 |
| point O | 70 | 76 | 63 |

TABLE 2-continued

|  | pyriminobac-methyl | bensulfuron-methyl | mefenacet |
|---|---|---|---|
| Average (%) | 79.5 | 84.0 | 74.1 |
| Deviation (%) | 9.7 | 9.9 | 9.4 |
| Example 4 |  |  |  |
| point A | 88 (%) | 90 (%) | 74 (%) |
| point B | 80 | 93 | 75 |
| point C | 79 | 96 | 71 |
| point D | 85 | 85 | 69 |
| point E | 90 | 84 | 83 |
| point F | 93 | 91 | 75 |
| point G | 80 | 80 | 89 |
| point H | 76 | 89 | 90 |
| point I | 83 | 91 | 72 |
| point J | 84 | 82 | 73 |
| point K | 91 | 86 | 87 |
| point L | 71 | 77 | 69 |
| point M | 63 | 81 | 84 |
| point N | 66 | 72 | 66 |
| point O | 68 | 85 | 65 |
| Average (%) | 79.8 | 85.5 | 76.1 |
| Deviation (%) | 11.7 | 7.5 | 11.0 |

TABLE 3

|  | pyriminobac-methyl | bensulfuron-methyl | mefenacet |
|---|---|---|---|
| Comparison Example 1 |  |  |  |
| point A | 90 (%) | 91 (%) | 74 (%) |
| point B | 81 | 99 | 70 |
| point C | 77 | 83 | 84 |
| point D | 94 | 87 | 70 |
| point E | 81 | 74 | 75 |
| point F | 45 | 62 | 24 |
| point G | 54 | 81 | 63 |
| point H | 11 | 21 | 0 |
| point I | 13 | 3 | 19 |
| Average (%) | 60.7 | 66.8 | 53.2 |
| Deviation (%) | 52.4 | 49.5 | 57.0 |
| Comparison Example 2 |  |  |  |
| point A | 82 (%) | 82 (%) | 63 (%) |
| point B | 91 | 91 | 68 |
| point C | 73 | 88 | 71 |
| point D | 83 | 83 | 60 |
| point E | 80 | 91 | 59 |
| point F | 85 | 84 | 71 |
| point G | 16 | 28 | 0 |
| point H | 302 | 168 | 541 |
| point I | 41 | 33 | 7 |
| Average (%) | 94.8 | 83.1 | 104.4 |
| Deviation (%) | 86.0 | 48.3 | 158.9 |

TABLE 4

|  | Example 1 | Example 2 | Example 3 | Example 4 | Comp. Ex. 1 | Comp. Ex. 2 |
|---|---|---|---|---|---|---|
| point A | 5.0 | 5.0 | 5.0 | 5.0 | 5.0 | 5.0 |
| point B | 5.0 | 5.0 | 5.0 | 5.0 | 5.0 | 5.0 |
| point C | 4.8 | 5.0 | 5.0 | 4.9 | 5.0 | 5.0 |
| point D | 5.0 | 5.0 | 4.9 | 5.0 | 5.0 | 5.0 |
| point E | 5.0 | 4.9 | 5.0 | 5.0 | 5.0 | 5.0 |
| point F | 5.0 | 5.0 | 5.0 | 5.0 | 3.6 | 5.0 |
| point G | 5.0 | 5.0 | 5.0 | 4.8 | 5.0 | 2.5 |
| point H | 4.8 | 4.9 | 4.9 | 5.0 | 2.9 | 5.0 |
| point I | 5.0 | 4.8 | 5.0 | 5.0 | 2.5 | 2.6 |
| point J |  |  | 5.0 | 5.0 |  |  |
| point K | 4.9 | 5.0 |  |  |  |  |
| point L | 5.0 | 4.9 |  |  |  |  |
| point M | 5.0 | 5.0 |  |  |  |  |
| point N | 4.8 | 4.8 |  |  |  |  |
| point O | 5.0 | 5.0 |  |  |  |  |

As shown in Table 1 and Table 2, in examples of the present invention, spreadability of the agrochemically active ingredient is excellent and the expected effect of the agrochemically active ingredient can be realized in a paddy field where algae are growing, but comparison examples are poor in spreadability of the ingredient, especially the effect of the agrochemically active ingredient at the point where algae exist is insufficient.

According to the present invention, when labor-saving scattering (applying) is performed even in a paddy field where algae are growing, or where roots of rice are growing to some extent, spreadability of the agrochemically active ingredient is excellent and it is possible to obtain the expected effect of the agricultural chemicals.

That is, when a formulation of the present invention containing granules of 3 mm or more in particle diameter in large quantity is used, it becomes possible to scatter (apply) an agricultural chemicals in an extremely labor-saving manner onto a paddy field, for instance, from a small scale of 30 are or less to a large scale of several hectare or so by selecting a method of application suitable for the condition of the paddy field to be applied in a form such as direct scattering from a levee without entering into a paddy field, or scattering from a radio-controlled helicopter or the like controlled from a levee.

What is claimed is:

1. A uniformly spreadable granular agricultural chemicals formulation comprising an agrochemically active ingredient, wherein the formulation:
   is in the form of granules,
   has a particle-size distribution such that 80% or more of the granules have a particle diameter of 3 mm or more,
   has floatability on the surface of paddy water, and
   breaks down on the water surface within 30 minutes,
   wherein said floatability is imparted to said formulation by incorporating a floatable carrier therein.

2. The uniformly spreadable granular agricultural chemicals formulation according to claim 1, further comprising at least one surfactant.

3. The uniformly spreadable granular agricultural chemicals formulation according to claim 1, further comprising 0.3 parts by weight to 6 parts by weight of water for 100 parts by weight of the agricultural chemicals formulation.

4. A method of applying the uniformly spreadable granular agricultural chemicals formulation as claimed in claim 1, the process comprising:
   applying the uniformly spreadable granular agricultural chemicals formulation on 5% to 50% of the total area of the paddy field from a levee at a distance of 1 m or more.

5. The uniformly spreadable granular agricultural chemicals formulation according to claim 1, further comprising water.

6. The uniformly spreadable granular agricultural chemicals formulation according to claim 1, wherein said agrochemically active ingredient is selected from the group consisting of herbicide, fungicide, insecticide, plant growth regulator and mixtures thereof.

7. The uniformly spreadable granular agricultural chemicals formulation according to claim 6, wherein said formulation comprises at least one herbicide selected from the group consisting of 2,4,6,-trichlorphenyl-4'-nitrophenylether, 2-methyl-4-chlorophenoxy-thioacetic acid-s-ethyl, α-(2-naphthoxy)propionanilide, 5-(2,4-dichlorophenoxy)-2-nitrobenzoate methyl, S-(4-chlorbenzyl)N,N-diethylthiocarbamate, S-benzyl-1,2-dimethlpropyl(ethyl)thiocarbamate, S-ethylhexahydro-1 H-azepin-1-carbothioate, S-1-methyl-1-phenylethyl-piperidine-1-carbothioate, O-3-tert-butylphenyl-6-methoxy-2-pyridyl(methyl)thiocarbamate, 2-chloro-2',6'-diethyl-N-(butoxymethyl)acetanilide, 2-chloro-2',6'-diethyl-N-(2-propoxyethyl)acetanilide, (RS)-2-bromo-N-(α,α-dimethylbenzyl)-3,3-dimethylbutylamide, 2-benzothiazol-2-yloxy-N-methylacetanilide, 1-(α,α-dimethylbenzyl)-3-(paratryl)urea, methyl-α-(4,6-dimethoxypyrimidine-2-ylcarbamoylsulfamoyl)-O-toluate(bensulfuronmethyl), 1-(2-cloroimidazo[1,2-a]pyridine-3-ylsulfonyl)-3-(4,6-dimethoxypyrimidine-2-yl)urea, ethyl-5-(4,6-dimethoxypyrimidine-2-ylcarbamoylsulfamoyl)-1-methylpyrasol-4-carboxylate, 2methythio-4,6-bis (ethylamino)-s-triazine, 2-methylthio-4,6-bis (isopropylamino)-s-triazine, 2-methylthio-4-ethylamino-6-(1,2-dimethylpropylamino)-s-triadine, 2,4-dichlorophenyl-3'-methoxy-4'-nitrophenylether, 5-tert-butyl-3-(2,4-dichoro-5-isopropoxyphenl)-1,3,4-oxadiazorin-2-one, 4-(2,4-dichlorobenzoyl)-1,3-dimethyl-5-pyrazoryl-p-toluensulfonate, 2-[4-(2,4-dichlorobenzoyl)-1,3-dimethylpyrazole-5-yloxy]acetophenone, (RS)-2-(2,4-dichloro-m-tolyloxy)propionanilide, 2-[4-[2,4-dichloro-m-toluoyl]-1,3-dimethylpyrazole-5-yloxy]-4'-methylacetophenon, S,S'-dimethyl-2-difluoromethyl-4-isobutyl-6-trifluoromethylpyridine-3,5-dicarbithioate, 2-chloro-N-(3-methoxy-2-thenyl)-2',6'-dimethylacetanilide, n-butyl-(R)-2-[4-(2-fluoro-4-cyanophenoxy)phenoxy]propionate, 3-[1-(3,5-dichlorphenyl)-1-methylethyl]-2,3-dihydro-6-methyl-5-phenyl-4H-1,3-oxazine-4-one, 3-(4-chloro-5-cyclopentyloxy-2flyorophenyl)-5-isopropyridene-1,3-oxazolidine-2,4-dione, 1-(diethylcarbamoyl)-3-(2,4,6-trimethylphenylsulfonyl)-1,2,4-triazole, N-{[(4,6-dimethoxypyrimidine-2-yl) aminocarbonyl]}-1-methyl-4-(2-methyl-2H-tetrazole-5-yl), methyl 2-[(4,6-dimethoxypyrimidine-2-yl)oxy]-6-[(E)-1-(methoxyimino) ethyl]benzoate and mixtures thereof.

8. The uniformly spreadable granular agricultural chemicals formulation according to claim 6, wherein said formulation comprises at least one fungicide selected from the group consisting of O,O-diisopropyl-S-benzylthiophosphate, 3'-isopropoxy-2-methylbenzanilide, α,α,α-trifluoro-3'-isopropoxy-O-toluanilide, 3,4,5,6-tetrachloro-N-(2,3-dichlorophenyl)phthalamid acid, 1-(4-chlorobenzyl)-1-cyclopentyl-3-phenylurea, 6-(3,5-dichloro-4-methylphenyl)-3(2H)-pyridazinone, methyl-N-(2-methoxyacetyl)-N-(2,6-xylyl)-DL-alaninate, (E)-4-chloro-α,α,α-trifluoro-N-( 1-imidazole-1-yl-2-propoxyethylidene)-o-toluidine, kasugamycin, baridamicine, 3-aryloxy-1,2-benzoisothiazole-1,1-dioxyd, diisopropyl-1,3-dithiolan-2-ylidene-malonate, 5-methyl-1,2,4-triazoro[3,4-b] benzothiazole, 1,2,5,6-tetrahydropylolo[3,2, 1-ij]chinoline-4-one, 5-ethyl-5,8-dihydro-8-oxo[1,3]dioxolo[4,5-g] chinoline-7-carboxylic acid, (Z)-2'-methylacetophenone-4, 6-dimethylpyrimidin-2-ylhydrazone 4,5,6,7-tetrachlorophthalide, 3-(3,5-dichlorophenyl)-N-isopropyl-2, 4-dioxoimidazolidine-1-carboxyamide and mixtures thereof.

9. The uniformly spreadable granular agricultural chemicals formulation according to claim 6, wherein said formulation comprises at least one insecticide selected from the group consisting of O,O-dimethyl-O-(3-methyl-4-nitrophenyl) thiophosphate, (2-isopropyl-4-methylpyrimidyl-6)-diethylthiophosphate, 1-naphthyl-N-methylcarbamate, O,O-diethyl-O-(3-oxo-2-phenyl-2H-pyridadine-6-yl) phosphorothioate, O,O-dimethyl-O-3,5,6-trichloro-2-pyridylphosphorothioate, dimethyldicarbethoxyethyldithiophosphate, O,O-dimethyl-S-(N-methylcarbamoylmethyl) dithiophosphate, O,O-dipropyl-O-4-methylthiophenylphosphate, O,S-dimethyl-N-acetylphosphoroamidethioate, ethylparanitrophenylthiono benzene phosphonate, 2-secondary-butylphenyl-N-methylcarbamate, 2,3-dihydro-2,2-dimethyl-7-benzo[b]flanyl-N-dibutylaminothio-N-methylcarbamate, ethyl-N-[2,3-dihydro-2,2-dimethylbenzoflan-7-yloxycarbonyl(methyl) aminothio]-N-isopropyl-β-alanynate, (RS)-α-cyano-3-phenoxybenzyl-(RS)-2,2-dichloro-1-(4-ethoxyphenyl) cyclopropane carboxylate, 2-(4-ethoxyphenyl)-2-methylpropyl-3-phenoxybenzyl-ether, 1,3-bis (carbamoylthio)-2-(N,N-dimethylamino)propane hydrochloride, 5-dimethylamino-1,2,3-trithian oxalate, S,S '-2-dimethylamino trimethylene-di(benzenthiosulfonate) (bensultap), 2-tert-butylimino-3-isopropyl-5-phenyl-1,3,5,6 tetrahydro-2H-1,3,5-thiadiazine-4-one and mixtures thereof.

10. The uniformly spreadable granular agricultural chemicals formulation according to claim 6, wherein said formulation comprises at least one plant growth regulator selected from the group consisting of 4'-chloro-2'-(α-hydroxybenzyl) isonicotinanilide, (2RS, 3RS)-1-(4-chlorophenyl)-4,4-dimethyl-2-(1H-1,2,4-triazole-1yl)pentane-3-ol, (E)-(S)-1-(4-chlorophenyl)-4,4-dimethyl-2-(1H-1,2,4-triazole-1-yl) penta-1-ene-3-ol and mixtures thereof.

11. The uniformly spreadable granular agricultural chemicals formulation according to claim 2, wherein the formulation comprises 0.1 parts by weight to 30 parts by weight of the surfactant per 100 parts by weight of the formulation.

12. The uniformly spreadable granular agricultural chemicals formulation according to claim 1, further comprising a binder and at least one organic solvent.

13. The uniformly spreadable granular agricultural chemicals formulation according to claim 1, wherein the particle diameter is from 3 mm to 20 mm.

14. The uniformly spreadable granular agricultural chemicals formulation according to claim 1, wherein the formulation comprises from 0.1 parts by weight to 70 parts by weight of the active ingredient per 100 parts by weight of the formulation.

15. The uniformly spreadable granular agricultural chemicals formulation according to claim 12 wherein the formulation comprises 0.01 parts by weight to 10 parts by weight of the binder per 100 parts by weight of the formulation and 10 parts by weight to 200 parts by weight of the organic solvent per 100 parts by weight of the active ingredient.

16. The uniformly spreadable granular agricultural chemicals formulation according to claim 1, wherein the floatable carrier is at least one material selected from the group consisting of pearlite derived from pearlstone or obsidian, foamed shirasu derived from shirasu, filite obtained by calcination of aluminosilicates, microbaloon which is made by foaming sodium silicate or borax, pumice, granular diatmite, granular activated carbon, wood powder, cork powder, kenaf pieces, phenol microbaloon made from phenol resin, echo-sphere made from epoxy resin, polyurethane foam made from polyurethane, microsphere made from polyacrylonitrile, and fly ash obtained as a by-product when performing thermal power generation.

17. The uniformly spreadable granular agricultural chemicals formulation according to claim 1, which contains no wax-like substance.

* * * * *